United States Patent
Kumar (10) Patent No.: US 10,957,435 B2
(45) Date of Patent: Mar. 23, 2021

(54) COMPUTER SYSTEM AND METHOD FOR GENERATING TRIGGER ALERTS TO MAXIMIZE INTERACTIONS WITH HEALTHCARE PROVIDERS

(71) Applicant: AstraZeneca AB, Södertälje (SE)

(72) Inventor: Kishore Kumar, Wilmington, DE (US)

(73) Assignee: ASTRAZENECA AB, Sodertalje (SE)

( * ) Notice: Subject to any disclaimer, the term of this patent is extended or adjusted under 35 U.S.C. 154(b) by 132 days.

(21) Appl. No.: 16/110,530

(22) Filed: Aug. 23, 2018

(65) Prior Publication Data

US 2019/0066830 A1 Feb. 28, 2019

Related U.S. Application Data

(60) Provisional application No. 62/550,092, filed on Aug. 25, 2017.

(51) Int. Cl.
  *G16H 20/10* (2018.01)
  *G16H 80/00* (2018.01)
  *G16H 10/60* (2018.01)

(52) U.S. Cl.
  CPC ............. *G16H 20/10* (2018.01); *G16H 10/60* (2018.01); *G16H 80/00* (2018.01)

(58) Field of Classification Search
  CPC .............................................. G06Q 50/22–24
  See application file for complete search history.

(56) References Cited

U.S. PATENT DOCUMENTS

| | | | |
|---|---|---|---|
| 7,395,216 B2* | 7/2008 | Rosenfeld | G06Q 50/22 705/2 |
| 2002/0032582 A1 | 3/2002 | Feeney, Jr. et al. | |
| 2004/0002872 A1 | 1/2004 | Wright | |
| 2004/0049506 A1* | 3/2004 | Ghouri | G06Q 30/02 |
| 2006/0129427 A1 | 6/2006 | Wennberg | |
| 2006/0206011 A1 | 9/2006 | Higgins et al. | |
| 2007/0112598 A1 | 5/2007 | Heckerman et al. | |
| 2009/0177495 A1 | 7/2009 | Abousy et al. | |

(Continued)

OTHER PUBLICATIONS

Tanner, Adam, "This Little-Known Firm Is Getting Rich Off Your Medical Data" https://fortune.com/2016/02/09/ims-health-privacy-medical-data/ (Year: 2016).*

(Continued)

*Primary Examiner* — Neal Sereboff
(74) *Attorney, Agent, or Firm* — Lee Sullivan Shea & Smith LLP (57) ABSTRACT

A pharmaceutical company may employ a computer system that is configured to train a machine learning model for predicting a next time in the future at which a given type of treatment decision is likely to be made for a patient, use the trained machine learning model to analyze anonymized patient data for patients treated by a given health care provider (HCP) in order to predict a next time in the future at which the given HCP is likely to make a given type of treatment decision for at least one patient, and then responsively generate a trigger alert suggesting that the given HCP be visited prior to the predicted next time to deliver a message related to the given type of treatment decision, which may in turn be delivered to a target of the trigger alert.

20 Claims, 4 Drawing Sheets

(56) References Cited

U.S. PATENT DOCUMENTS

| | | | | |
|---|---|---|---|---|
| 2011/0288880 | A1* | 11/2011 | Waugh | G06Q 50/22 |
| | | | | 705/2 |
| 2011/0295621 | A1 | 12/2011 | Farooq et al. | |
| 2014/0257840 | A1* | 9/2014 | Cardone | G16H 10/60 |
| | | | | 705/2 |
| 2014/0337052 | A1* | 11/2014 | Pellini | G16H 10/20 |
| | | | | 705/3 |
| 2016/0354154 | A1* | 12/2016 | Ghouri | G06F 19/326 |
| 2018/0004902 | A1* | 1/2018 | Aronow | G06F 19/326 |
| 2018/0308569 | A1* | 10/2018 | Luellen | G16H 40/20 |
| 2019/0355472 | A1* | 11/2019 | Kutzko | G16H 20/10 |

OTHER PUBLICATIONS

Goodman, Bryce et al., European Union Regulations on Algorithmic Decision-Making and a "Right to Explanation", arXiv:1606.08813v3 [stat.ML], Aug. 31, 2016, pp. 1-9.

Palkoner, David, "Turning Data Into Insight: Event-Based Notifications Drive Improved Outcomes", Healthcare IT Oct. 10, 2014, http:www.healthcareitnews.com/blog/turning-data-insight-event-based-notitications-drive-improved-outcomes-0, retrieved from Internet Apr. 19, 2017, 4 pages.

\* cited by examiner

COMPUTER SYSTEM AND METHOD FOR GENERATING TRIGGER ALERTS TO MAXIMIZE INTERACTIONS WITH HEALTHCARE PROVIDERS

CROSS-REFERENCE TO RELATED APPLICATIONS

This application claims benefit under 35 U.S.C. § 119(e) of U.S. Provisional Application No. 62/550,092, filed Aug. 25, 2017. The above listed application is incorporated by reference herein in its entirety for all purposes.

BACKGROUND

Healthcare providers (HCPs), such as doctors, nurses, and the like, may treat patients who have various medical conditions. As part of treating a patient, an HCP may make various types of treatment decisions for that patient, many of which may involve the prescription of a given type of pharmaceutical product to a patient (e.g., a given type of drug). For example, after diagnosing a patient with a new medical condition, an HCP may make a treatment decision for the patient that involves prescription of a new pharmaceutical product. As another example, after determining that a patient's previously-diagnosed condition has changed (e.g. bettered or worsened) and/or that the patient has reported side effects, an HCP may make a treatment decision for the patient that involves switching the patient's prescription to a different pharmaceutical product. Many other examples of treatment decisions are possible as well.

Generally, when an HCP decides to prescribe a given type of pharmaceutical product as part of a treatment decision, the HCP may have many different options to choose from. Indeed, there may be many different pharmaceutical companies that offer pharmaceutical products of the given type, and these companies may be competing with one another for prescriptions of their respective product. To this end, a pharmaceutical company often employs representatives (e.g., sales representatives, a medical science liaisons (MSLs), Nurse Educators, Diagnostic liaisons, etc.) that are tasked with visiting HCPs and promoting advantages of the pharmaceutical company's products in an effort to influence HCPs to prescribe those products, which may in turn drive sales of the pharmaceutical company's products However, the interaction between a representative of a pharmaceutical company and an HCP tends to be limited in terms of the number of interactions, the length of the interactions, and what can be discussed during the interaction. For example, the discussions between a representative of a pharmaceutical company and an HCP typically cannot be patient-centric (e.g. may not specifically be based on the medical conditions that the HCP is treating and/or the types of treatment decisions that the HCP is making), but rather must be informational in nature. As a result of this limited interaction, it may be difficult for a representative of a pharmaceutical company to achieve the representative's primary goal, which is to influence the HCP to prescribe the pharmaceutical company's products to the HCP's patients thereby driving sales of those products. This is particularly the case for specialty markets, such as immunology, oncology, biologics, rare or orphan disease, etc., where HCPs tend to decide which pharmaceutical products to prescribe to their patients based on the HCP's preexisting loyalty to certain pharmaceutical companies and/or products.

Moreover, pharmaceutical companies currently have limited visibility as to when an HCP will be making treatment decisions for the HCP's patients, which is a key factor that may impact whether a representative of a pharmaceutical company will succeed in influencing the HCP to prescribe the company's products to the HCP's patients. For instance, if an HCP is likely to make a treatment decision that involves prescription of a given type of pharmaceutical product in the foreseeable future, then visiting the HCP shortly before the treatment decision to promote the advantages of a product of the given type that is offered by the company may maximize the chances that the HCP will prescribe the company's product as opposed to a competing product. On the other hand, if the HCP is not likely to make a treatment decision that involves prescription of a given type of product in the foreseeable future, then visiting the HCP to promote the company's product of the given type may not provide as much value.

OVERVIEW

Given the format and/or volume of anonymized patient data, it is presently difficult or impossible for a user (such as a representative of a pharmaceutical company) to derive information from such data that can be used to improve interactions with HCPs. Moreover, existing interfaces for accessing and viewing anonymized patient data fail to present such data in an intelligent or efficient way, which further inhibits a user's ability to derive information from anonymized patient data that can be used to improve interactions with HCPs.

To address these and other problems with existing technology, disclosed herein are new techniques for analyzing, summarizing, and presenting anonymized patient data that enable a platform to provide advanced insights into anonymized patient data, which may help a pharmaceutical company improve the productivity and efficiency of interactions with HCPs.

In one aspect, the platform may be configured to generate and present "trigger alerts," which are timely notifications intended for representatives of a given pharmaceutical company that suggest visits to HCPs that are likely to be making treatment decisions in the foreseeable future. The platform may be configured to generate trigger alerts in various manners.

According to one implementation, the platform may be configured to receive and ingest anonymized patient data for patients being treated by each of a plurality of different HCPs. This anonymized patient data may take various forms. As one example, an anonymized patient data set may comprise, for each of a plurality of patients that are included in the set, (1) anonymized identifying information for the patient, such as a unique identifier assigned to the given patient, indications of the given patient's age, gender, ethnicity, geographic area of residence (e.g., zip code, state, etc.), and/or payer type, and an identifier of the given patient's treating HCP, and (2) medical history information for the patient, such as information about different categories of events that have been recorded as part of the given patient's medical history (e.g., drug treatment events, surgery and/or radiation events, medical test events, diagnosis events, patient visit events, and/or side effect events). The anonymized patient data may take other forms as well.

After receiving and ingesting the anonymized patient data, the platform may perform an analysis of the anonymized patient data to determine whether each HCP of the plurality of HCPs is likely to make a given type of treatment decision for at least one patient in the foreseeable future (e.g., a treatment decision that is likely to involve a prescription of a given type of pharmaceutical product), and if so, predict the time at which the given type of treatment decision is likely to be made. The platform may perform this analysis in various manners.

According to one example, the platform may perform this analysis using a machine learning model that takes anonymized patient data for a given patient being treated by a given HCP as input and outputs a predicted time in the future when the given type of treatment decision is likely to be made for the given patient. According to another example, the platform may perform this analysis using a set of predefined rules that return a predicted time in the future when the given type of treatment decision is likely to be made for a given patient. The platform may perform this analysis in other manners as well.

Based on the analysis, the platform may predict that a given HCP of the plurality of HCPs is likely to make the given type of treatment decision for at least one patient at a given predicted time in the future. In response, the platform may then generate a trigger alert suggesting that the given HCP be visited prior to the given predicted time to deliver a message related to the given type of treatment decision. This trigger alert may comprise various information, examples of which include identifying information for the given HCP, information indicating a time for the suggested visit with the given HCP (e.g., a time sufficiently prior to the given predicted time), patient data for the at least one patient of the given HCP, and a recommended message to be delivered to the given HCP during the suggested visit in order to influence the given HCP to prescribe a pharmaceutical product offered by the given pharmaceutical company. The trigger alert may include other information as well.

After generating the trigger alert, the platform may then cause the trigger alert to be presented to a target of the trigger alert, such as a representative of the given pharmaceutical company that is tasked with interacting with the given HCP. For example, the platform may cause the trigger alert to be sent to a client device associated with the trigger in the form of a text message, e-mail, instant message, or a notification that is presented via a native application or a web application running on the client device, among other possibilities.

In practice, the platform may to cause the trigger alert to be presented to the target at various different times. As one example, the platform may cause the trigger alert to be presented to the target as soon as the trigger alert is generated. As another example, the platform may cause the trigger alert to be presented to the target at a time that is determined based on the given predicted time when the treatment decision is likely to be made by the given HCP (e.g., a particular number of days before the treatment decision is likely to be made by the given HCP). The platform may cause the trigger alert to be presented to the target at other times as well.

In addition to generating and causing trigger alerts to be presented, the platform may also be configured to prioritize and/or consolidate trigger alerts in various manners. For instance, the platform may prioritize and/or consolidate multiple trigger alerts for the same patient, multiple trigger alerts for different patients being treated by the same HCP, and/or multiple trigger alerts for different HCPs being visited by same target.

Advantageously, these trigger alerts may provide a representative of the given pharmaceutical company with visibility as to when HCPs serviced by the representative will be making certain treatment decisions that involve prescriptions of pharmaceutical products offered by the given pharmaceutical company, which may enable the representative to deliver the right message to the HCPs at the right time such that the representative can maximize the chances that the HCPs will prescribe the pharmaceutical company's products (as opposed to a competing pharmaceutical products).

In another aspect, the platform may be configured to provide a visualization of the medical history for a given patient, which may further assist a representative of the given pharmaceutical company to maximize interactions with HCPs. In one example, the medical history visualization for a given patient may include a timeline of events that have occurred in the given patient's medical history, which are broken into different categories of events (e.g., drug treatment events, surgery and/or radiation events, medical test events, diagnosis events, patient visit events, and side effect events) as well as different types of events within each category. In addition, the indicator for each respective event in the given patient's history may be color-coded to indicate the medical specialty associated with the event.

The platform may also enable a user to manipulate the medical history visualization in various manners. For example, the platform may enable to a user to "zoom" into a particular area of the medical history visualization, which may provide more granular detail regarding the medical events in that particular area of the visualization. As another example, the platform may enable a user to filter the categories, types, and/or dates of events that are presented on the medical history visualization. Other examples are possible as well.

In yet another aspect, the platform may be configured to identify patients to be recruited for a given clinical trial. The platform may perform the identification in various manners.

According to one implementation, the platform may first be configured with a set of criteria for identifying patients to be recruited for the given clinical trial, which may take various forms. In one example, the set of criteria may specify certain medical events that need to have occurred in a patient's past (e.g., a surgery event, a chemotherapy event, etc.) and/or an age requirement for the patient. In another example, the set of criteria may specify certain combinations and/or sequences of medical events that need to have occurred in a patient's past. Other examples are possible as well.

After being configured with the set of criteria, the platform may then periodically apply the set of criteria to the anonymized patient data that is received from the data source. The platform may perform this function at various times. As one example, the platform may perform this function in response to receiving new anonymized patient data from the data source. As another example, the platform may perform this function in accordance with a schedule. As yet another example, the platform may perform this function in response to receiving a user request. Other examples are possible as well.

Based on the application of the set of criteria to the anonymized patient data, the platform may identify one or more patients that satisfy the set of criteria, and thus appear to be eligible for the given clinical trial. In turn, the platform may identify the treating HCP for each of the identified one or more patients, and then for each identified HCP, the platform may generate and provide a notification to a target suggesting that the HCP be contacted to recruit one or more of the HCP's patients for the given clinical trial. Such a notification may be generated and provided in a similar manner to a trigger alert.

Accordingly, in one aspect, disclosed herein is a method carried out by a computer system (e.g., a platform operating by or on behalf of a given pharmaceutical company) that involves (a) receiving, from a data source, anonymized patient data for patients treated by each of a plurality of HCPs, (b) analyzing the anonymized patient data for patients treated by each HCP of the plurality of HCPs to determine whether each HCP is likely to make a given type of treatment decision for at least one patient in the foreseeable future, where the given type of treatment decision is likely to involve a prescription of a given type of pharmaceutical product, (c) based on the analysis, predicting that a given HCP of the plurality of HCPs is likely to make the given type of treatment decision for at least one patient at a given predicted time in the future, (d) in response to predicting that the given HCP is likely to make the given type of treatment decision for at least one patient at the given predicted time in the future, generating a trigger alert suggesting that the given HCP be visited prior to the given predicted time to deliver a message related to the given type of treatment decision, and (d) causing the trigger alert to be sent to a client device associated with a target of the trigger alert (e.g., a representative of a given pharmaceutical company that offers a pharmaceutical product of the given type of pharmaceutical product).

The anonymized patient data may take various forms. According to one example, anonymized patient data may include anonymized identifying information and medical history information for each patient, where the medical history information for each patient includes information about one or more of drug treatment events, surgery events, radiation events, medical test events, diagnosis events, patient visit events, and side effect events. The anonymized patient data may take other forms as well.

Further, the analysis of the anonymized patient data for patients treated by each HCP of the plurality of HCPs may be carried out in various manners, including through the use of a machine learning model or a set of predefined rules.

Further yet, the trigger alert may take various forms. According to one example, the trigger alerts may include one or more of an indication of a time for the suggested visit with the given HCP, patient data for the least one patient of the given HCP, and/or a recommended message to be delivered by the target during the suggested visit with the given HCP.

In another aspect, disclosed herein is a computer system that includes at least one processor, a tangible, non-transitory computer-readable medium, and program instructions stored on the tangible, non-transitory computer-readable medium that are executable by the at least one processor to cause the computer system to carry out the functions disclosed herein.

In yet another aspect, disclosed herein is non-transitory computer-readable medium having program instructions stored thereon that are executable to cause a computer system to carry out the functions disclosed herein.

One of ordinary skill in the art will appreciate these as well as numerous other aspects in reading the following disclosure.

DETAILED DESCRIPTION

The following disclosure makes reference to the accompanying figures and several exemplary embodiments. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. Example Network Configuration

Figure 1:
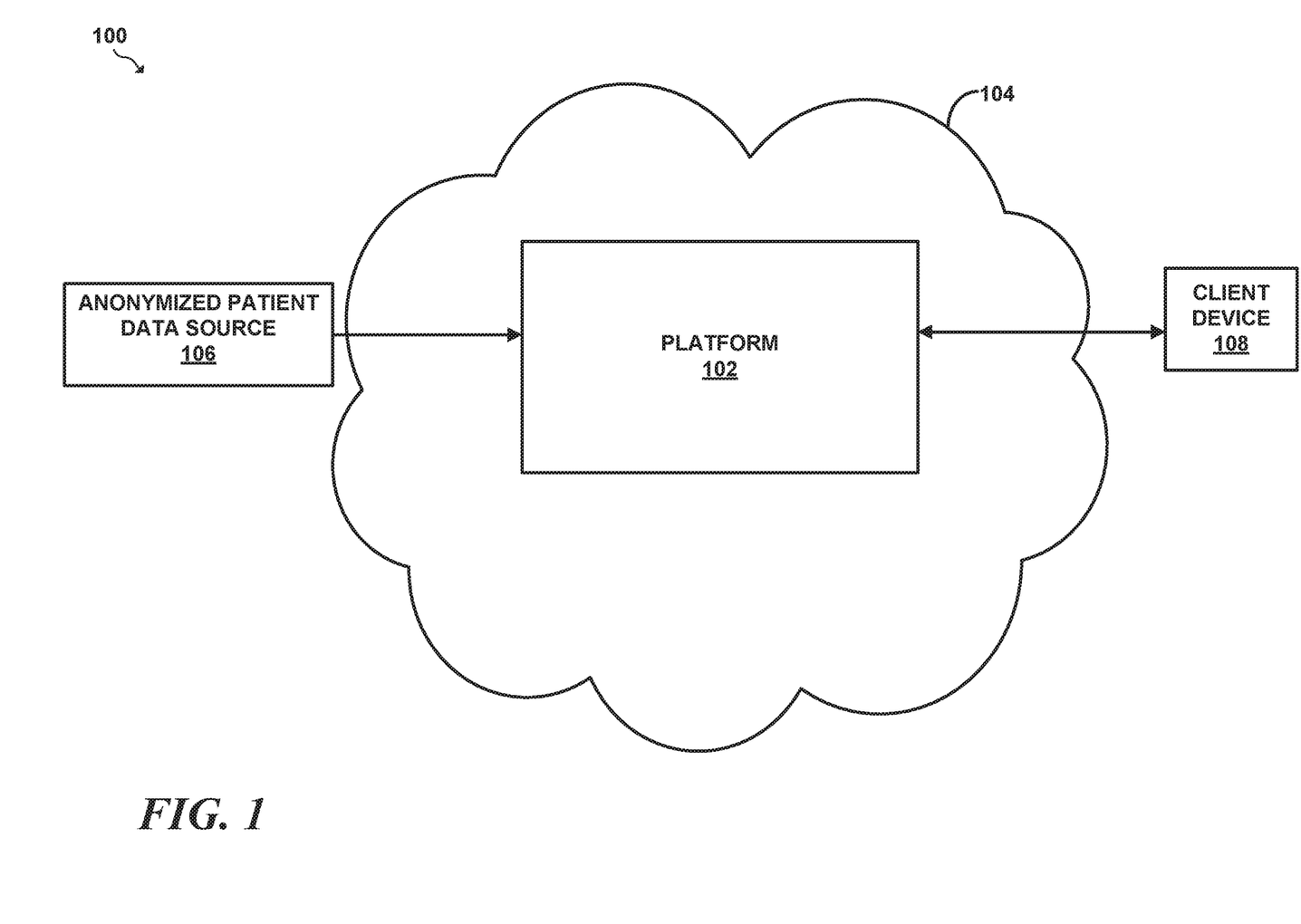
FIG. 1 is a block diagram of an example network configuration.

FIG. 1 is a conceptual diagram of a network configuration 100. As shown, network configuration 100 comprises at its core a platform 102, which may communicate via a communication network 104 with one or more patient data sources, such as anonymized patient data source 106, as well one or more client devices, such as client device 108. In practice, platform 102 may be operated by (or on behalf of) a given pharmaceutical company that is in the business of selling pharmaceutical products. It should be understood that the network configuration may include various other systems as well.

Broadly speaking, platform 102 may take the form of any one or more computer systems that are configured to perform the operations disclosed herein, which include ingesting and analyzing anonymized patient data in order to generate trigger alerts suggesting visits to HCPs that are likely to be making treatment decisions in the foreseeable future, provide medical history visualizations for patients, and identify patients to recruit for clinical trials. In this respect, platform 102 may comprise one or more servers (or the like) having hardware components and software components that are configured to carry out one or more of the functions disclosed herein for receiving, ingesting, processing, and/or analyzing, anonymized patient data. In practice, these computing systems may be located in a single physical location or distributed amongst a plurality of locations, and may be communicatively linked via a system bus, a communication network (e.g., a private network, private cloud, hybrid cloud, or the like), or some other communication mechanism. Platform 102 may take other forms as well. Platform 102 is discussed in further detail below with reference to FIG. 2.

As shown in FIG. 1, platform 102 may be configured to communicate, via communication network 104, with one or more data sources and/or client devices and in network configuration 100. For example, platform 102 may receive anonymized patient data, via communication network 104, from anonymized patient data source 106. As another example, platform 102 may send data defining a trigger alert, via communication network 104, for receipt by a client device such as client device 108. Platform may engage in other types of communication via communication network 104 as well.

In general, communication network 104 may include one or more computing systems and network infrastructure configured to facilitate transferring data between platform 102 and the one or more data sources and/or client devices. Communication network 104 may be or may include one or more Wide-Area Networks (WANs) and/or Local-Area Networks (LANs), which may be wired and/or wireless and may support secure communication. In some examples, communication network 104 may include one or more cellular networks and/or the Internet, among other networks. Further, communication network 104 may operate according to one or more communication protocols, such as LTE (Long Term Evolution), CDMA (Carrier Division Multiple Access), GSM, LPWAN, WiFi (e.g. the 802.11x family of protocols from the Institute of Electrical and Electronics Engineers (IEEE), Bluetooth, Fibre Channel, Ethernet (e.g. the IEEE 802.3x family of standards), WDM (Wavelength Division Multiplexing), HTTP/S (Secure/Hypertext Transport Protocol), TLS (Transport Level Security), TCP (Transmission Control Protocol), UDP (Universal Datagram Protocol), ATM, FDDI, CoAP (Constrained Application Protocol)/DTLS (datagram Transport Layer Security), and/or the like.

Although communication network 104 is shown as a single network, it should be understood the communication network 104 may include multiple, distinct networks that are themselves communicatively linked. Further, in example cases, communication network 104 may facilitate secure communications between network components (e.g., via encryption or other security measures). Communication network 104 could take other forms as well.

Although not shown, it should also be understood that the communication path between platform 102, the one or more patient data sources, and the one or more client devices may include one or more intermediate systems. For example, anonymized patient data source 106 may send anonymized patient data to one or more intermediary systems, and platform 102 may then be configured to receive the anonymized patient data from the one or more intermediary systems. As another example, platform 102 may communicate with client device 108 via one or more intermediary systems, such as a host server (not shown). Many other configurations are also possible.

In general, anonymized patient data source 106 may comprise one or more computing systems (e.g., servers or the like) configured to collect, aggregate, process, store, and/or provide anonymized patient data. In this respect, anonymized patient data source 106 may take various forms. As one possible example, anonymized patient data source 106 may be an anonymized patient data source maintained by a third-party data provider and/or other data aggregators. Other examples are possible as well. (It should also be understood that anonymized patient data source 106 may include multiple different data sources maintained by the same or different data providers).

The anonymized patient data provided by anonymized patient data source 106 may take various forms. At a high-level, an anonymized patient data set may comprise, for each of a plurality of patients that are included in the set, (1) anonymized identifying information for the patient and (2) medical history information for the patient.

The anonymized identifying information for a given patient may include various information, examples of which may include a unique identifier assigned to the given patient, indications of the given patient's age, gender, ethnicity, geographic area of residence (e.g., zip code, state, etc.), and/or payer type, and an identifier of the given patient's treating HCP, among other possible information. In this respect, the anonymized patient data may be organized and/or grouped in various different manners, including by age, by gender, by geographic area, by payer status, and/or by HCP. The anonymized identifying information for a given patient may include other types of information and/or take other forms as well.

Likewise, the medical history information for a patient may include various information. As one example, the medical history information for a given patient may include information about different categories of events that have been recorded as part of the given patient's medical history, such as drug treatment events (e.g., prescriptions of different types of pharmaceuticals), surgery and/or radiation events, medical test events, diagnosis events (e.g., primary or secondary diagnosis), patient visit events (e.g., office visits, inpatient or outpatient hospital visits, emergency room visits, etc.), and/or side effect events for instance. The information about each such event may include an indication of the event category (e.g., drug treatment, surgery/radiation, test, etc.), the particular type of event within that event category (e.g., the particular type of pharmaceutical that was prescribed, the particular type of surgery, radiation, or test that occurred, etc.), the date of the event, and/or the medical specialty associated with the event (e.g., primary care provider (PCP), hospital, surgery, oncology, urology, etc.), among other possibilities.

As another example, if the given patient is currently undergoing treatment for a particular medical condition (e.g., a disease such as cancer), the medical history information may include information about the given patient's treatment, such as the date when the given patient began the treatment, the total amount of time that the given patient has been undergoing the treatment, the current stage of the given patient's treatment (e.g., the current line of therapy in the treatment of cancer), and/or the dates when the given patient entered different stages of the treatment, for instance. The medical history information for a given patient may include other types of information and/or take other forms as well.

Further, the anonymized patient data provided by anonymized patient data source 106 may be arranged in various different formats. Examples of these formats may include: XML, HTML, or other markup formats. The patient data may be represented in other formats as well.

Although not shown, platform 102 may also have access to various other data types and/or data sources as well. For instance, platform 102 may have access to one or more data sources that provide additional data about HCPs of interest. This additional data about HCPs of interest may take various forms, examples of which may include data indicating accounts and/or hospitals with which HCPs are affiliated, data indicating details of past interactions with HCPs, data indicating how HCPs have treated patients in the past, data indicating the propensity of HCPs to use different classes of pharmaceutical products (e.g., different classes of drugs), and data indicating the accessibility of certain pharmaceutical products to HCPs (e.g., whether the HCP can access a drug through payers). Platform 102 may have access to other data types and/or other data sources as well.

Client device 108 may take the form of a computing system or device configured to access and enable a user (e.g., a sales representative) to interact with platform 102. To facilitate this, client device 108 may include hardware components such as a user interface, a network interface, a processor, and data storage, among other components, as well as software components such as a web browser that is capable of accessing a web application (e.g. via an API) provided by platform 102 or a native client application associated with platform 102, among other examples. Representative examples of client device 108 may include a desktop computer, a laptop, a netbook, a tablet, a smartphone, a personal digital assistant (PDA), or any other such device now known or later developed.

In accordance with the present disclosure, client device 108 may be associated with a representative of the given pharmaceutical company, such as a sales representative, a medical science liaison (MSL), a Nurse Educator, or a Diagnostic liaison, as examples.

It should be understood that network configuration 100 is one example of a network in which embodiments described herein may be implemented. Numerous other arrangements are possible and contemplated herein. For instance, other network configurations may include additional components not pictured and/or more or fewer of the pictured components.

II. Example Platform

An example platform will now be described with reference to FIG. 2. Platform 102 may have a configuration similar that of the example platform illustrated with reference to FIG. 2.

Figure 2:
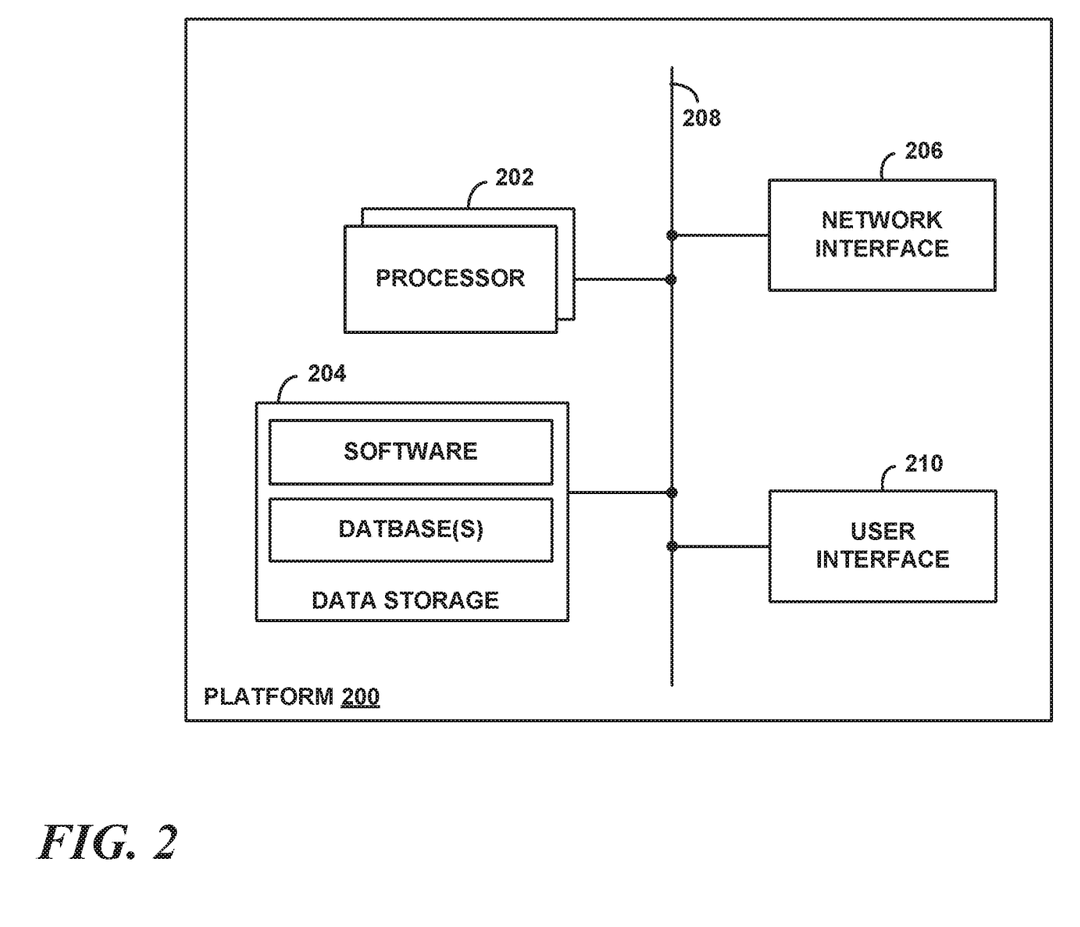
FIG. 2 is a block diagram of an example platform.

FIG. 2 is a simplified block diagram illustrating some components that may be included in an example platform 200 from a structural perspective. In line with the discussion above, example platform 200 may generally comprise one or more computer systems (e.g., one or more servers), and these one or more computer systems may collectively include at least a processor 202, data storage 204, and a network interface 206, all of which may be communicatively linked by a communication link 208 such as a system bus, network, or other connection mechanism. In addition, example platform 200 may also include a user interface 210. Example platform 200 may include other components and/or take other forms as well.

Processor 202 may include one or more processors and/or controllers, each of which may take the form of a general- or special-purpose processor or controller. In particular, in example implementations, processor 202 may take the form of one or more microprocessors, microcontrollers, application-specific integrated circuits, digital signal processors, or the like.

In turn, data storage 204 may comprise one or more non-transitory computer-readable storage mediums, examples of which may include volatile storage mediums such as random-access memory, registers, cache, etc. and non-volatile storage mediums such as read-only memory, a hard-disk drive, a solid-state drive, flash memory, an optical-storage device, etc.

As shown in FIG. 2, data storage 204 may be provisioned with software components that enable the platform 200 to carry out the functions disclosed herein. These software components may generally take the form of program instructions that are executable by processor 202, and may be arranged together into applications, software development kits, toolsets, or the like. In addition, data storage 204 may also be provisioned with one or more databases that are arranged to store data related to the functions carried out by the platform, examples of which include time-series databases, document databases, relational databases (e.g., MySQL), key-value databases, graph databases, and/or other databases employed in a big data environment, among others. The one or more databases may also provide for poly-glot storage.

Network interface 206 may be configured to facilitate wireless and/or wired communication between platform 200 and various network components coupled to communication network 104, such as anonymized patient data source 106, and/or client device 108. As such, network interface 206 may take any suitable form for carrying out these functions, examples of which may include an Ethernet interface, a serial bus interface (e.g., Firewire, USB 2.0, etc.), a chipset and antenna adapted to facilitate wireless communication, and/or any other interface that provides for wired and/or wireless communication. Network interface 202 may also include multiple network interfaces that support various different types of network connections. Other configurations are possible as well.

In some embodiments, example platform 200 may also include a user interface 210 that is configured to facilitate user interaction with platform 200 and may also be configured to facilitate causing platform 200 to perform an operation in response to user interaction. User interface 210 may include or provide connectivity to various input components, examples of which include touch-sensitive interfaces, mechanical interfaces (e.g., levers, buttons, wheels, dials, keyboards, etc.), and other input interfaces (e.g., microphones). Additionally, user interface 210 may include or provide connectivity to various output components, examples of which may include display screens, speakers, headphone jacks, and the like. Other configurations are possible as well.

In other embodiments, users may interact with example platform 200 via a client device that is communicatively coupled to example platform 200 via a communication network and the platform's network interface. Other configurations are possible as well.

III. Example Platform Operations

Example operations of the platform discussed above in connection with FIGS. 1-2 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

A. Providing Trigger Alerts

Figure 3:
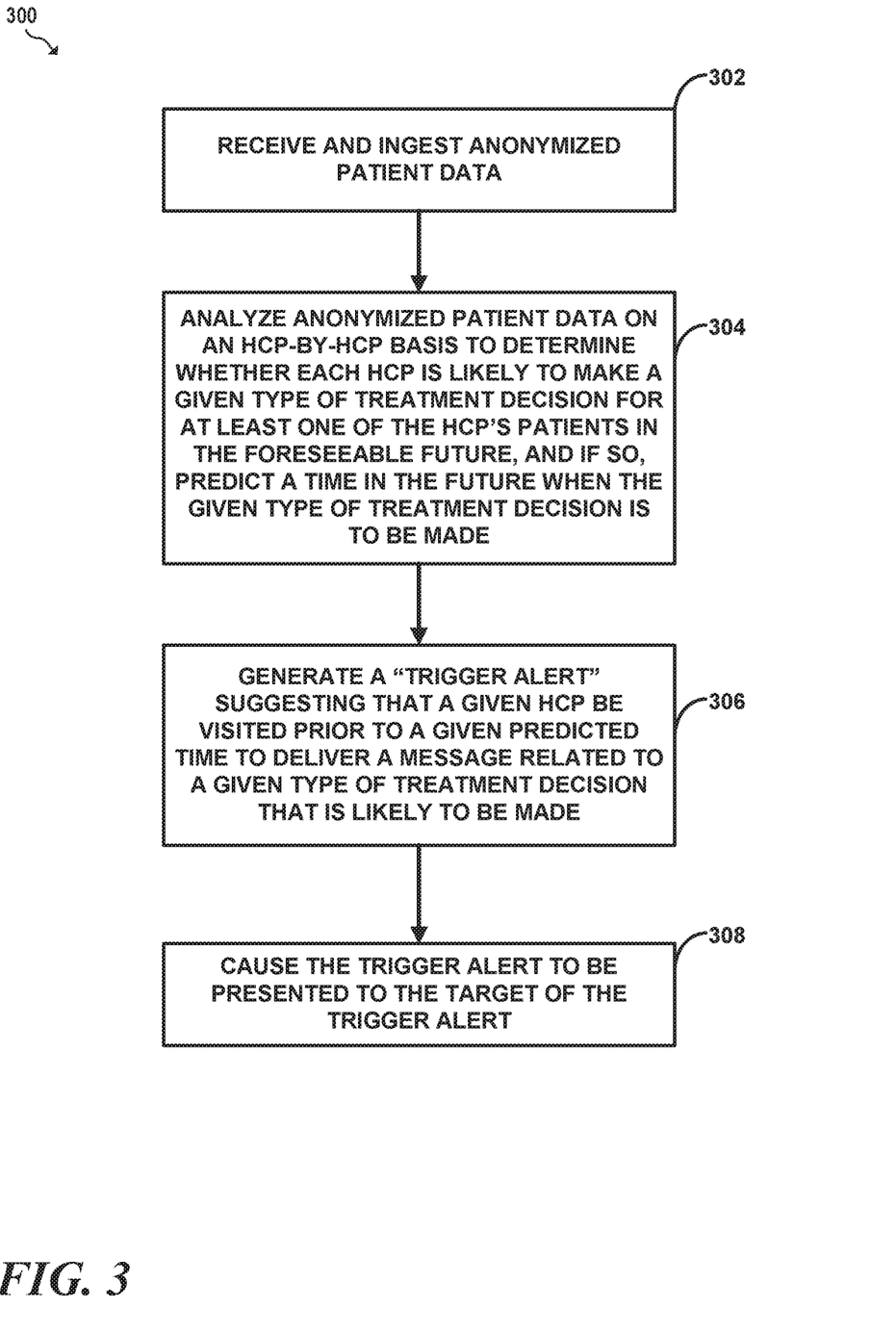
FIG. 3 is a flow diagram illustrating an example of a process for generating trigger alerts.

In one aspect, platform 102 may be configured to generate and present trigger alerts, which may enable a given pharmaceutical company to increase the chances of having HCPs prescribe pharmaceutical products offered by the given pharmaceutical company. FIG. 3 provides a flow diagram 300 to illustrate example functions that can be carried out in accordance with one example process for generating and presenting trigger alerts. For purposes of illustration, the example functions are described as being carried out by platform 102, but it should be understood that computing systems or devices other than platform 102 may perform the example functions. One of ordinary skill in the art will also appreciate that the flow diagram 300 is provided for sake of clarity and explanation and that other combinations of functions may be utilized to generate trigger alerts. The example functions shown in the flow diagram may also be rearranged into different orders, combined into fewer blocks, separated into additional blocks, and/or removed based upon the particular embodiment, and other example functions may be added.

At block 302, platform 102 may receive and ingest anonymized patient data from at least one data source, such as anonymized patient data source 106. In line with the discussion above, this anonymized patient data may include, for each of a plurality of patients that are the subject of the anonymized patient data, (1) anonymized identifying information for the patient (e.g., a unique identifier, age, gender, ethnicity, payer status, treating HCP, etc.) and (2) medical history information for the patient (e.g., medical event information, treatment plan information, etc.). However, the anonymized patient data may include other information and take other forms as well.

The function of receiving anonymized patient data from anonymized patient data source 106 may take various forms. According to one implementation, platform 102 may "subscribe" to a service provided by anonymized patient data source 106, in which case anonymized patient data may periodically be "pushed" from anonymized patient data source 106 to platform 102 in accordance with its subscription to this service. According to another implementation, platform 102 may be configured to periodically request and receive (i.e., "pull") anonymized patient data from anonymized patient data source 106 (e.g., in accordance with a scheduler). Platform 102 may receive anonymized patient data from anonymized patient data source 106 in other manners as well.

Further, the function of ingesting the anonymized patient data received from anonymized patient data source 106 may take various forms. For instance, the function of ingesting the anonymized patient data from data source 106 may involve one or more pre-processing operations, such as parsing, mapping, re-organizing, cleaning, and/or de-duplicating the anonymized patient data from data source 106, among other options. Additionally, after performing the one or more pre-processing operations, the function of ingesting the anonymized patient data from data source 106 may involve storing the anonymized patient data in one or more data stores (e.g. databases or flat files). Additionally yet, the function of ingesting the anonymized patient data from data source 106 may involve integrating the anonymized patient data from data source 106 with other anonymized patient data, such as anonymized patient data received from another source and/or anonymized patient data that was previously ingested and stored by platform 102, which may improve the quality and/or accuracy of the anonymized patient data. For example, different data sources may provide different patient data records for the same patients, in which case platform 102 may integrate the different patient data records for each such patient together in order to produce a "master" patient data record for each such patient. Other examples are possible as well. The function of ingesting the anonymized patient data received from anonymized patient data source 106 may involve other operations as well.

In some embodiments, as part of the ingestion process, platform 102 may reorganize the anonymized patient data such that it is grouped on an HCP-by-HCP basis. For instance, using the identification of treating HCP included in the anonymized identifying data, platform 102 may arrange the patient data for all patients being treated by a first HCP into a first group of patient data associated with that first HCP, arrange the patient data for all patients being treated by a second HCP into a second group of patient data associated with that first HCP, etc. Platform 102 may perform this function for all HCPs identified within the anonymized patient data, or only a subset of the HCPs identified within the anonymized patient data (e.g., only HCPs that are of interest to the given pharmaceutical company with which platform 102 is associated).

In other embodiments, platform 102 may maintain the organization of the anonymized patient data as it is received from the anonymized patient data source 106, in which case platform 102 may be configured to search, filter, and/or sort the stored anonymized patient data based on HCP identity (among other data fields) such that platform 102 can analyze the anonymized patient data on an HCP-by-HCP basis.

Platform 102 may also be configured to generate derived data from the anonymized patient data. This derived data may take various forms. As examples, the derived data may include data related to the sphere of influence of HCPs relative to one another, treatment pathways, and/or the decision process of building regimens. Many other types of derived data may be generated as well.

At block 304, platform 102 may analyze the anonymized patient data on an HCP-by-HCP basis to determine whether each HCP of interest is likely to make a given type of treatment decision for at least one of the HCP's patients in the foreseeable future (e.g., a treatment decision that may involve prescribing a given type of pharmaceutical product that is offered by the given pharmaceutical company), and if so, predict a time in the future when the given type of treatment decision is to be made. In this respect, the HCPs of interest may include each HCP identified within the anonymized patient data, or only a subset of the HCPs identified within the anonymized patient data. For example, platform 102 may be configured to perform an analysis of anonymized patient data only for a predefined subset of HCPs that are of interest to the given pharmaceutical company with which platform 102 is associated (e.g., HCPs that have previously met with the pharmaceutical company's representatives, have previously prescribed the given pharmaceutical company's pharmaceutical products, and/or have attended the given pharmaceutical company's events). Other examples are possible as well.

Platform 102 may access anonymized patient data for each HCP of interest in various manners. In one example, platform 102 reorganize the anonymized patient data during ingestion such that it is grouped on an HCP-by-HCP basis (as described above), in which case platform 102 may simply access the group of anonymized patient data for a given HCP. In another example, platform 102 may use the identity of given HCP to search, filter, and/or sort the stored anonymized patient data in order to access anonymized patient data for a given HCP. Other examples are possible as well. Regardless of how platform 102 accesses the anonymized patient data for a given HCP, this anonymized patient data may generally include a respective set of anonymized patient data for each of one or more patients being treated by the given HCP. In some implementations, platform 102 may also use a date filter while accessing the anonymized patient data for each HCP of interest, such that platform 102 only accesses anonymized patient data from a particular window of time (e.g., data regarding medical events that have occurred over the past 5 years).

The analysis that platform 102 performs on the anonymized patient data accessed for each HCP of interest may take various forms. In one embodiment, platform 102 may perform this analysis using a machine learning model that is configured to predict (1) whether a given type of treatment decision is likely to be made for a patient at some time in the future, and (2) if so, the time at which the given type of treatment decision is likely to be made. Such a machine learning may take various forms.

Generally, a machine learning model used by platform 102 may take anonymized patient data for a given patient as the model's input (e.g., medical history data and perhaps also identifying information such as age, gender, etc.), and may output a predicted time in the future when the given type of treatment decision is likely to be made for the given patient. The given type of treatment decision may take various forms. As one possible example, a machine learning model may be used to predict a time in the future when a decision will be made to transition a patient from a first line of cancer therapy to a second line of cancer therapy, which is likely to involve the prescription of a cancer drug. Machine learning models for predicting the timing of various other types of treatment decisions may be used as well.

Further, such a machine learning model may be defined using various machine learning techniques, including but not limited to deep learning techniques, supervised machine learning techniques, and/or unsupervised machine learning techniques. According to one implementation, platform 102 may begin the process of defining a machine learning model for predicting at time at which a given type of treatment decision will be made by analyzing a set of historical patient data (which may be referred to as "training data") to identify past occurrences of the given type of treatment decision. Platform 102 may identify these past occurrences of the given type of treatment decision in various manners.

In some cases, the historical patient data may include "labels" that indicate when instances of the given type of treatment decision have previously been made by HCPs, in which case platform 102 may identify the past occurrences of the given type of treatment decision based on these labels. In other cases, the historical patient data may not include "labels" for the given type of treatment decision, in which case platform 102 may identify past occurrences of the given type of treatment decision based on other data. For example, platform 102 may be programmed with a rule specifying that a given sequence of medical events experienced by a patient indicates the occurrence of the given type of treatment decision, in which case platform 102 may identify occurrences of the given type of treatment decision by detecting instances where a patient experience the given sequence of medical events.

For each identified past occurrence of the given type of treatment decision, platform 102 may then identify a respective set of historical patient data that is associated with each identified past occurrence of the given type of treatment decision. This respective set of historical patient data may take various forms. As one example, the respective set of historical patient data associated with a past occurrence of the given type of treatment decision for a given patient may include medical events information for the given patient that preceded the occurrence of the given type of treatment decision, including but not limited to the categories, types, and dates of any medical events that preceded the treatment decision for the given patient. As another example, the respective set of historical patient data associated with a past occurrence of the given type of treatment decision for a given patient may include certain identifying information for the given patient, such as the given patient's age, gender, etc. Other examples are possible as well.

After identifying the sets of historical patient data associated with past occurrences of the given type of treatment decision, platform 102 may analyze the identified historical patient data to define a relationship between (a) the anonymized patient data and (b) the timing of a future treatment decision of the given type, where this relationship may then be embodied into the machine learning model. For instance, an example machine learning model may embody a relationship between medical events occurring in a patient's past (among other anonymized patient data) and the timing of a future treatment decision of the given type relative to those medical events. Platform 102 may perform this analysis using any supervised learning technique now known or later developed, including but not limited to linear regression.

The machine learning model used by platform 102 may take many other forms and be defined in many other manners as well. For instance, while the inputs of the example machine learning model are described above in terms of anonymized patient data received from data source 106, it should be understood that the machine learning model may additionally or alternatively be defined to receive other data as inputs, such as data derived from the anonymized patient data received from data source 106 (which may be referred to as "features") and/or additional data about the HCPs of interest (e.g., data indicating accounts and/or hospitals with which HCPs are affiliated, details of past interactions with HCPs, how HCPs have treated patients in the past, propensity of HCPs to use different classes of pharmaceutical products, accessibility of certain pharmaceutical products to HCP, etc.).

Further, while the example machine learning model is described above as a single-stage model that takes anonymized patient data for a given patient as the model's input and outputs a predicted time in the future when the given type of treatment decision is likely to be made for the given patient, it should be understood that the machine learning model may comprise multiple stages. For example, the machine learning model defined and executed by platform 102 may comprise a two-stage model in which (1) the first stage of the model takes anonymized patient data for a given patient as the model's input and outputs a value indicating a likelihood of whether the given type of treatment decision will be made for the given patient in the foreseeable future (e.g., within a 1 month period in the future) and (2) if the likelihood value output by the first stage satisfies a threshold, the second stage of the model is triggered to determine a predicted time in the future when the given type of treatment decision is likely to be made for the given patient. According to this example, the input to the model's second stage may take various forms, examples of which may include the anonymized patient data that is input into the model's first stage and/or a subset thereof (e.g., a particular subset of the medical events that have occurred in the given patient's past), and perhaps also additional data about the given patient's treating HCP (e.g., historical data related to how the HCP has treated patients in the past), among other examples. Other examples of multi-stage models are possible as well.

Further yet, while the example machine learning model is described above as being defined using a supervised machine learning technique, as noted above, various other machine learning techniques may be used as well, including other forms of supervised machine learning, deep learning, and/or unsupervised learning, as examples.

Still further, it should be understood that the machine learning model may be periodically updated (or "retrained") based on updated training data.

The function of using a machine learning model to analyze the anonymized patient data for each HCP of interest may also take various forms. According to one implementation, platform 102 may take the respective set of anonymized patient data for each respective patient being treated by a given HCP and input it into the machine learning model, which may in turn output a predicted time in the future when the given HCP is likely to make the given type of treatment decision for the respective patient. This output may take various forms. As one example, the output may be represented as a calendar date. As another example, the output may be represented as an amount of time into the future (e.g., a number of hours, days, weeks, etc.). As yet another example, if the respective set of anonymized patient data does not indicate that the given type of treatment decision is likely to be made for the respective patient in the foreseeable future (e.g., the likelihood value determined by the model does not satisfy a threshold), the output may be an indicator that no time has been predicted (e.g., a "null," "N/A," or the like), or the model may not output anything at all. The output of the machine learning model may take other forms as well.

Based on the output of the machine learning model for each of the given HCP's one or more patients, platform 102 may determine whether the given HCP is likely to make the given type of treatment decision for at least one of the given HCP's patients in the foreseeable future. If so, platform 102 may generate a trigger alert for the given HCP (or perhaps multiple trigger alerts if it is determined that the given HCP is likely to make the given type of treatment decision for multiple of the given HCP's patients in the foreseeable future), which is described in further detail below. Platform 102 may perform a similar process for each other HCP of interest.

While the above embodiment is described in terms of using one machine learning model that predicts the timing of one type of treatment decision, it should be understood that platform 102 may be configured to execute a plurality of different machine learning models, each of which is used to predict a different type of treatment decision. For example, platform 102 may be configured to input the anonymized patient data for each HCP of interest into a first machine learning model for predicting a time in the future when a first type of treatment decision is likely to be made, a second machine learning model for predicting a time in the future when a second type of treatment decision is likely to be made, and so on. In this respect, each different machine learning model may take a form and be defined in a manner similar to that described above. Further, in practice, platform 102 may be configured to execute the plurality of machine learning models in parallel, in series, or some combination thereof.

In another embodiment, platform 102 may perform the analysis of the anonymized patient data for each HCP of interest using a set of predefined rules that enable platform 102 to predict a time in the future when a given type of treatment decision is likely to be made. Such a set of predefined rules may take various forms.

Generally, the set of predefined rules may include Boolean logic rules, such as "if-then" type rules, each specifying that if the anonymized patient data for a patient satisfies one or more conditions, then a given type of a treatment decision is likely to be made at a given time in the future. For example, such a rule may specify that if a patient has experienced a given type of diagnosis event, then a given type of treatment decision is likely to be made a given amount of time (e.g., a given number of days, weeks, months, etc.) after that diagnosis event. As another example, such a rule may specify that if a patient has experienced a threshold number of a given type of event (e.g., toxicity event) within a given window of time, then a given type of treatment decision is likely to be made a given amount of time (e.g., a given number of days, weeks, months, etc.) after the threshold number has been reached. As yet another example, such a rule may specify that if a patient experiences a given sequence of medical events, then the given type of treatment decision is likely to be made a given amount of time (e.g., a given number of days, weeks, months, etc.) after the last event in that sequence. The set of predefined rules may take various other forms as well (including the possibility that different rules associated with the given type of treatment decision may return predictions of different times in the future).

To illustrate with a real-world example, platform 102 may be configured with a set of predefined rules for predicting a time in the future when a decision will be made to transition a patient undergoing bladder cancer treatment from a first line of therapy to a second line of therapy, which is likely to involve the prescription of a cancer drug. In this example, one possible rule may specify that if a patient has a cystectomy, undergoes GemCarbo chemotherapy, and then thereafter suffers a urinary tract infection (UTI) event, then a decision to transition the patent from a first line of cancer therapy to a second line of cancer therapy is likely to be made a given amount of time (e.g., 3 months) after the UTI event. A set of predefined rules for predicting when a decision will be made to transition a patient undergoing bladder cancer treatment from a first line of therapy to a second line of therapy may take various other forms as well.

Further, the set of predefined rules for predicting when a given type of treatment decision is likely to be made may be defined in various manners. As one example, platform 102 may define the set of predefined rules based on user input. As another example, platform 102 may define the set of predefined rules based on an analysis of historical anonymized patient data, such as the training data described above. The set of predefined rules may be defined in various other manners as well.

The function of using a set of predefined rules to analyze the anonymized patient data for each HCP of interest may also take various forms. According to one implementation, platform 102 may apply the set of predefined rules to the respective set of anonymized patient data for each respective patient being treated by a given HCP, to determine whether the given HCP is likely to make the given type of treatment decision for at least one of the given HCP's patients in the foreseeable future. If so, platform 102 may generate a trigger alert for the given HCP (or perhaps multiple trigger alerts if it is determined that the given HCP is likely to make the given type of treatment decision for multiple of the given HCP's patients in the foreseeable future), which is described in further detail below. Platform 102 may perform a similar process for each other HCP of interest.

While the above embodiment is described in terms of using one set of predefined rules for predicting the timing of one type of treatment decision, it should be understood that platform 102 may be configured to execute a plurality of different sets of predefined rules, each of which is used to predicts a different type of treatment decision. For example, platform 102 may be configured to apply a first set of predefined rules for predicting a time in the future when a first type of treatment decision is likely to be made, a second set of predefined rules for predicting a time in the future when a second type of treatment decision is likely to be made, and so on. In this respect, each different set of predefined rules may take a form and be defined in a manner similar to that described above. Further, in practice, platform 102 may be configured to apply the different sets of predefined rules in parallel, in series, or some combination thereof.

Platform 102 may be configured to perform the analysis of anonymized patient data to predict whether and when treatment decisions are likely to be made in various other manners as well. For example, instead of performing the analysis on an HCP-by-HCP basis, platform 102 may be configured to perform the analysis on a patient-by-patient basis without first grouping patients by HCP, in which case platform 102 may be configured to consolidate trigger alerts for different patients being treated by the same HCP. Other examples are possible as well.

Further, it should be understood that platform 102 may be configured to perform this analysis at various different times. As one example, platform 102 may perform the analysis in response to receiving new anonymized patient data from anonymized patient data source 106. As another example, platform 102 may perform the analysis in accordance with a schedule. As yet another example, platform 102 may perform the analysis in response to receiving a user request. Other examples are possible as well.

At block 306, if platform 102 determines that a given HCP is likely to make a given type of treatment decision for at least one patient of the given HCP at a given predicted time in the future, platform 102 may generate a "trigger alert," which is a notification suggesting that the given HCP be visited prior to the given predicted time to deliver a message related to the given type of treatment decision that is likely to be made. The target of this trigger alert may be a representative of the given pharmaceutical company that is tasked with interacting with the given HCP, such as a sales representative, an MSL, a Nurse Educator, or a Diagnostic liaison for instance. (While the trigger alerts described herein suggest HCP visits, it be understood that the trigger alerts may suggest other types of interactions with the HCP as well, such as telephone calls or electronic communications).

This trigger alert may include various information. As one possibility, the trigger alert may include information about the given HCP, such as the given HCP's name, address, suspected role in treatment, and specialty for instance. In this respect, platform 102 may access this information about the given HCP from a database or the like.

As another possibility, the trigger alert may indicate a time for the suggested visit with the given HCP. This indication may take various forms. As one example, platform 102 may determine and include a suggested time for the suggested visit that is sufficiently in advanced of the given predicted time (e.g., one or more days before the given predicted time). As another example, platform 102 may include the given predicted time in the trigger alert along with a note indicating that the given HCP should be visited prior to the given predicted time. As yet another example, platform 102 may include a suggested timeframe of the visit that is measured from the time when the trigger alert is generated (e.g., a suggestion to visit the given HCP within a given number of days of receiving the trigger alert). The trigger alert may indicate the time for the suggested visit with the given HCP in other manners as well.

As yet another possibility, the trigger alert may include certain patient data for the at least one patient of the given HCP that has some relevance to the given type of treatment decision that is likely to be made by the given HCP. For example, the trigger alert may include an indication of one or more past medical events experienced by the at least patient that led platform 102 to determine that the given HCP is likely to make the treatment decision for the at least one patient at the given predicted time, which may be referred to as "drivers." As another example, the trigger alert may include anonymized identifying information for the at least one patient, such as the patient's age, gender, payer status, etc. Other examples are possible as well.

As still another possibility, the trigger alert may include a recommended message to be delivered during the suggested visit with the given HCP to cause the given HCP to prescribe a pharmaceutical product offered by the given pharmaceutical company (e.g., talking points for the visit). This recommended message may take various forms. According to one possible implementation, the recommended message may identify a given pharmaceutical product offered by the given pharmaceutical company and emphasize aspects of the given pharmaceutical product that are relevant to the given type of treatment decision that the HCP is predicted to make, such as safety, efficacy, toxicity, side effect profile, and/or cost favorability. The recommended message may include other information and/or take other forms as well.

In practice, platform 102 may determine the recommended message to include in the trigger alert in various manners. In one embodiment, platform 102 may predefine a recommended message that generally corresponds to the given type of treatment decision, in which case platform 102 may be configured to include that predefined recommended message by default in each trigger alert that is generated when the given type of treatment decision is predicted to occur. For example, if the given type of treatment decision is a decision to transition a patient from a first line of cancer therapy to a second line of cancer therapy and the given pharmaceutical company offers a cancer drug brand of the type that is likely to be prescribed as part of this transition, platform 102 may predefine a recommended message emphasizing the aspects of the given pharmaceutical company's cancer drug brand that are most relevant to patients transitioning from a first line of cancer therapy to a second line of cancer therapy.

In another embodiment, platform 102 may be configured to generate a recommended message that is tailored for the particular trigger alert being generated. Platform 102 may generate such a recommended message in various manners.

According to one implementation, platform 102 may first identify which product offered by the given pharmaceutical company should be recommended in view of the upcoming treatment decision that is likely to be made by the given HCP. Platform 102 may make this identification in various manners. As one example, platform 102 may identify the product to recommend based on data that indicates a correlation between the given type of treatment decision and which of the given pharmaceutical company's product(s) are of the type that is likely to be prescribed as part of given type of treatment decision. In this respect, the given pharmaceutical company may only offer a single product of the type that is likely to be prescribed as part of given type of treatment decision, in which case platform 102 may simply identify that single product as the one to recommend to the given HCP. On the other hand, it is possible that the given pharmaceutical company may offer multiple different products of the type that is likely to be prescribed as part of given type of treatment decision, in which case platform 102 may rely on other factors to identify which product to recommend to the given HCP. Examples of such factors may include the given HCP's propensity to use the different products, the given HCP's access to the different products, the at least one patient's access to the different products, and/or the given pharmaceutical company's own internal prioritization of the different products, among other possibilities. (It should also be understood that, in some implementations, platform 102 could identify multiple different products to recommend to the given HCP).

After identifying which product offered by the given pharmaceutical company should be recommended, platform 102 may then identify which aspects of the product should be emphasized to the given HCP. Platform 102 may perform this identification in various manners as well.

As one example, platform 102 may identify which aspects of the product should be emphasized to the given HCP based on anonymized patient data for the at least one patient of the given HCP. For instance, based on medical events data for the at least one patient (among other patient data), platform 102 may determine that certain aspects of the product are particularly relevant to the at least one patient (e.g., efficacy and/or toxicity), in which case platform 102 may specifically identify these aspects of the product as the ones to emphasize to the given HCP.

As another example, platform 102 may identify which aspects of the product should be emphasized to the given HCP based on data about the given HCP that is indicative of the given HCP's preferences and/or tendencies, such as data indicating details of past interactions with the given HCP and/or data indicating how the given HCP has treated patients in the past, among other possibilities.

As yet another example, platform 102 may identify which aspects of the product should be emphasized to the given HCP based on data about the particular product that has been identified, such as data indicating positive aspects of the product that should generally be emphasized irrespective of HCP or the HCP's at least one patient (e.g., brand strategy information).

Platform 102 may identify which aspects of the product should be emphasized to the given HCP based on other factors and/or in other manners as well.

Once platform 102 identifies which product offered by the given pharmaceutical company should be recommended and which aspects of the product should be emphasized, platform 102 may then generate a recommended message that includes that information and is to be included in the trigger alert.

The trigger alert generated by platform 102 may include other information, take other forms, and/or be generated in other manners as well.

At block 308, after generating the trigger alert suggesting that the given HCP be visited prior to the given predicted time to deliver a message related to the given type of treatment decision that is likely to be made, platform 102 may cause the trigger alert to be presented to the target of the trigger alert. Platform 102 may carry out this function in various manners.

According to one implementation, platform 102 may first identify the target of the trigger alert. For example, platform 102 may identify one or more representatives of the given pharmaceutical company as the target of the trigger alert, such as a representative that has been tasked with interacting given HCP and/or a representative that is responsible for the geographic territory in which the given HCP is located. As part of this identification, platform 102 may also take into account the availability of the given pharmaceutical company's representatives (e.g., platform 102 may have access to the representatives' schedules). Platform 102 may identify the target of the trigger alert in other manners as well.

Platform 102 may then cause the trigger alert to be sent to a client device associated with the identified target, such as client device 108. For example, platform 102 may cause the trigger alert to be sent to the target's client device in the form of a text message, e-mail, instant message, or a notification that is presented via a native application or a web application running on the client device, as some examples. In turn, the client device may present the trigger alert to the target via the client device's user interface.

Further, platform 102 may be configured to cause the trigger alert to be presented to the target at various different times. As one example, platform 102 may be configured to cause the trigger alert to be presented to the target as soon as the trigger alert is generated. As another example, platform 102 may be configured to cause the trigger alert to be presented to the target at a time that is determined based on the given predicted time when the treatment decision is likely to be made by the given HCP. For instance, platform 102 may cause the trigger alert to be presented to the target a particular amount of time (e.g., a particular number of days) before the treatment decision is likely to be made by the given HCP. Platform 102 may be configured to cause the trigger alert to be presented to the target at other times as well, although in general, platform 102 will preferably cause the trigger alert to be presented to the target at a time that is far enough in advance of the given predicted time that the target has sufficient time to take action in response to the trigger event.

In addition to generating and causing trigger alerts to be presented, platform 102 may also be configured to prioritize and/or consolidate trigger alerts in various manners. This prioritization and/or consolidation of trigger alerts may take various different forms.

As one possibility, the platform's analysis of the anonymized patient data for a given patient may lead platform 102 to generate multiple trigger alerts for the given patient. In this respect, platform 102 may prioritize which trigger alert for the given patient to present to the target based on factors such as the date of the last trigger alert for the patient, the time sensitivity of each trigger alert (e.g., the length of time between when the trigger alert is generated and when the treatment decision is likely to be made), the confidence level associated with each trigger alert, and the precision associated with each trigger alert, as examples. Additionally or alternatively, if multiple trigger alerts for a given patient have similar characteristics (e.g., the same type of treatment decision to be made at or around the same time), platform 102 may consolidate the multiple trigger alerts into a single trigger alert.

As another possibility, the platform's analysis of the anonymized patient data for a given HCP may lead platform 102 to generate multiple trigger alerts for the given HCP. In this respect, platform 102 may prioritize which trigger alert for the given HCP to present to the target based on factors such as the time sensitivity of each trigger alert, the confidence level associated with each trigger alert, the precision associated with each trigger alert, and the probability that each trigger alert will lead to a prescription of a pharmaceutical product offered by the given pharmaceutical company, as examples. Additionally or alternatively, if multiple trigger alerts for a given HCP have similar characteristics (e.g., the same type of treatment decision to be made at or around the same time), platform 102 may consolidate the multiple trigger alerts into a single trigger alert.

As yet another possibility, the platform's analysis of the anonymized patient data for a plurality of HCPs that are managed by the same target may lead platform 102 to generate multiple trigger alerts for the target. In this respect, platform 102 may prioritize which trigger alert to present to the target based on factors such as the patient potential associated with each HCP, past field activity and/or feedback associated with each HCP, time sensitivity of the trigger alerts, and the access and/or affinity associated with each HCP, among other examples. Additionally or alternatively, if multiple trigger alerts for a given target have similar characteristics (e.g., the same type of treatment decision to be made at or around same time), platform 102 may consolidate the multiple trigger alerts into a single trigger alert.

Platform 102 may also be configured to prioritize and/or consolidate trigger alerts in other manners as well.

After being presented with a trigger alert suggesting that a given HCP be visited prior to a given predicted time to deliver a message related to a given type of treatment decision that is likely to be made, a target of the trigger alert (e.g., a representative of the given pharmaceutical company such as a sales representative, an MSL, a Nurse Educator, or a Diagnostic liaison) may then schedule a visit with the given HCP and use the information provided in the trigger alert to help increase the chances that the given HCP may prescribe a pharmaceutical product offered by the given pharmaceutical company.

Accordingly, the foregoing process may take anonymized patient data—which is typically difficult or impossible for a user to meaningfully evaluate due to the format and/or volume of such data—and use that anonymized patient data as a basis for generating and presenting a target user with timely, actionable insights regarding HCP interactions that take the form of trigger alerts delivered in advance of predicted HCP treatment decisions. In this way, the foregoing process may help a representative of pharmaceutical company to improve interactions with HCPs, among other benefits.

B. Providing A Medical History Visualization

Figure 4:
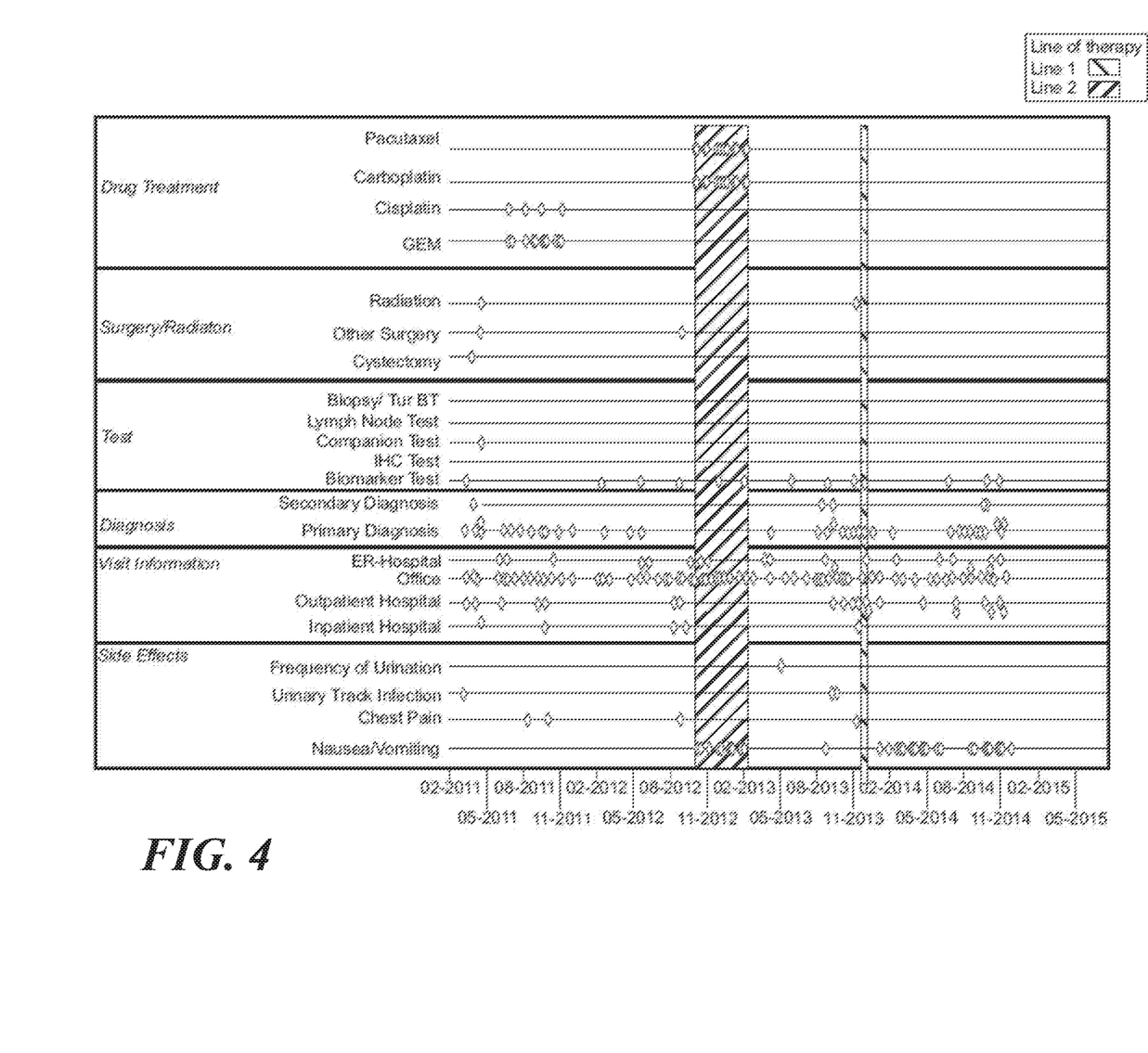
FIG. 4 is an example of a medical history visualization provided by the platform.

In another aspect, platform 102 may be configured to provide a new type of visualization of a patient's medical history. FIG. 4 shows one representative example of a medical history visualization that may be provided by platform 102 for a given patent. As shown, the example medical history visualization may include a timeline of events that have occurred in the given patient's medical history, which are broken into different categories of events as well as different types of events within each category. For example, FIG. 4 shows representative examples of event categories that may be included in the medical history visualization (e.g., drug treatment events, surgery and/or radiation events, medical test events, diagnosis events, patient visit events, and side effect events), as well as a few representative examples of event types that may be included each category. It should be understood that these example event categories and event types are merely provided for purposes of illustration, and that various other event categories and event types may be included in the medical history visualization as well. In addition, as shown, the medical history visualization may include indicators of the dates when the given patient entered different stages of the treatment, such as different lines of cancer therapy.

Although not shown, the medical history visualization may include other information about the given patient and his or her medical history as well. For example, the medical history visualization may include identifying information for the given patient, such as the given patient's unique identifier, the given patient's age, the given patient's gender, the given patient's treating HCP, etc. As another example, the indicator for each respective event in the given patient's history may be color-coded to indicate the medical specialty associated with the event. Other examples are possible as well.

Platform 102 may also enable a user to manipulate the medical history visualization in various manners. For example, platform 102 may enable to a user to "zoom" into a particular area of the medical history visualization, which may provide more granular detail regarding the medical events in that particular area of the visualization. As another example, platform 102 may enable a user to filter the categories, types, and/or dates of events that are presented on the medical history visualization. As yet another example, platform 102 may enable a user to switch the medical history visualization between different patients using a drop-down menu, a text entry box, a separate "patient list" screen, or the like. Platform 102 may enable a user to manipulate the medical history visualization in other manners as well.

In practice, platform 102 may generate the medical history visualization based on the anonymized patient data that is received from anonymized patient data source 106. Further, platform 102 may provide the medical history visualization via a graphical user interface that is presented on a client device, such as client device 108. In this respect, platform 102 may be configured to provide the medical history visualization for the given patient in response to receiving a request from client device 108 that included an identification of the given patient. Platform 102 may provide the medical history visualization in other manners as well.

Advantageously, the medical history visualization provided by platform 102 constitutes a new way of summarizing and presenting a patient's medical history that may help a representative of the given pharmaceutical company to improve interactions with HCPs, among other benefits.

C. Identifying Patients For Clinical Trials

In yet another aspect, platform 102 may be configured to identify patients to be recruited for clinical trials. Platform 102 may perform this identification in various manners.

According to one implementation, platform 102 may be configured with a set of criteria for identifying patients to be recruited for a given clinical trial. This set of criteria may take various forms. As one possibility, the set of criteria may specify certain categories and/or types of medical events that need to have occurred in a patient's past. For example, the set of criteria may specify that a qualifying patient has experienced at least one occurrence of each of a plurality of different types of medical events in the patient's past, such as at least one a surgery event, at least one chemotherapy event, etc. As another possibility, the set of criteria may specify certain sequence and/or timing requirements for the medical events that have occurred in the patient's past. For example, the set of criteria may specify not only that a patient has experienced two different types of events, but also that the one type of event occurred within a given period of time prior to the other type of event (e.g., a surgery event occurred within a given period of time prior to the chemotherapy event). As yet another possibility, the set of criteria may specify that the patient be at a given stage of treatment. As still another possibility, the set of criteria may specify an age, gender, and/or ethnicity requirement for the patient. Other examples are possible as well.

Further, the set of criteria may be defined in various manners. As one example, platform 102 may define the set of criteria based on user input. As another example, platform 102 may define the set of criteria based on an analysis of historical anonymized patient data. The set of criteria may be defined in various other manners as well.

After being configured with the set of criteria, platform 102 may then periodically apply the set of criteria to the anonymized patient data received from anonymized patient data source 106 (and/or data derived therefrom). Platform 102 may perform this function at various times. As one example, platform 102 may perform this function in response to receiving new anonymized patient data from anonymized patient data source 106. As another example, platform 102 may perform this function in accordance with a schedule. As yet another example, platform 102 may perform this function in response to receiving a user request. Other examples are possible as well.

Based on the application of the set of criteria to the anonymized patient data, platform 102 may identify one or more patients that satisfy the set of criteria, and thus appear to be eligible for the given clinical trial. In turn, platform 102 may identify the treating HCP for each of the identified one or more patients.

For each identified HCP, platform 102 may then generate and provide a notification to a target suggesting that the HCP be contacted to recruit one or more of the HCP's patients for the given clinical trial. Such a notification may be generated and provided in a similar manner to a trigger alert, which is described in detail above.

In addition to (or in alternative to) having platform 102 configured with a set of criteria for identifying patients to be recruited for a given clinical trial, platform 102 may provide a user interface (such as the medical history visualization described above) through which a user can search for and review patients to be recruited for the given clinical trial. For example, the medical history visualization may include an area where a user can input the set of criteria for identifying patients to be recruited for the given clinical trial. In turn, the medical history visualization may return a list of patients that satisfy the criteria, where each patient's medical history may then be viewed via the medical history visualization.

Advantageously, the foregoing techniques for identifying and presenting information regarding patients that qualify for clinical trials constitute another new way of summarizing and presenting anonymized patient data that may help a representative of the given pharmaceutical company to improve interactions with HCPs, among other benefits.

IV. Conclusion

Example embodiments of the disclosed innovations have been described above. Those skilled in the art will understand, however, that changes and modifications may be made to the embodiments described without departing from the true scope and sprit of the present invention, which will be defined by the claims.

Further, to the extent that examples described herein involve operations performed or initiated by actors, such as "humans", "operators", "users" or other entities, this is for purposes of example and explanation only. The claims should not be construed as requiring action by such actors unless explicitly recited in the claim language.

The invention claimed is:

1. A computer system comprising:
at least one processor;
a tangible, non-transitory computer-readable medium; and
program instructions stored on the tangible, non-transitory computer-readable medium that are executable by the at least one processor to cause the computer system to:
  apply one or more machine learning techniques to historical patient data associated with past occurrences of a given type of treatment decision in order to train a machine learning model that is configured to (i) receive anonymized patient data for a patient as input and (ii) predict a next time in the future at which the given type of treatment decision is likely to be made for the patient;
  receive, from a data source, anonymized patient data for patients treated by each of a plurality of healthcare providers (HCPs);
  analyze the anonymized patient data for the patients treated by each respective HCP of the plurality of HCPs by inputting the anonymized patient data for each respective patient treated by the respective HCP into the trained machine learning model, wherein the given type of treatment decision is likely to involve a prescription of a given type of pharmaceutical product;
  based on the analysis, predict at least one particular time in the future at which a given HCP of the plurality of HCPs is likely to make the given type of treatment decision for at least one patient;
  in response to predicting the particular time in the future at which the given HCP is likely to make the given type of treatment decision for the at least one patient, generate a trigger alert suggesting that the given HCP be visited prior to the particular time in the future to deliver a message related to the given type of treatment decision; and
  cause the trigger alert to be sent to a client device associated with a target of the trigger alert.

2. The computer system of claim 1, wherein the anonymized patient data comprises anonymized identifying information and medical history information for each patient.

3. The computer system of claim 2, wherein the medical history information for each patient comprises information about one or more of drug treatment events, surgery events, radiation events, medical test events, diagnosis events, patient visit events, or side effect events.

4. The computer system of claim 1, wherein the given type of treatment decision comprises a decision to transition a patient from one stage of treatment to another stage of treatment.

5. The computer system of claim 1, wherein the trigger alert indicates a time for the suggested visit with the given HCP.

6. The computer system of claim 1, wherein the trigger alert comprises patient data for the least one patient of the given HCP.

7. The computer system of claim 1, wherein the trigger alert comprises a recommended message to be delivered by the target during the suggested visit with the given HCP.

8. The computer system of claim 1, wherein the target comprises a representative of a given pharmaceutical company that offers a pharmaceutical product of the given type of pharmaceutical product.

9. The computer system of claim 1, wherein the program instructions that are executable by the at least one processor to cause the computer system to cause the trigger alert to be sent to the client device associated with the target of the trigger alert comprise program instructions stored on the tangible, non-transitory computer-readable medium that are executable by the at least one processor to cause the computer system to cause the trigger alert to be sent to the client device associated with the target of the trigger alert at a time that is determined based on the particular time in the future.

10. The computer system of claim 1, wherein the client device associated with the target of the trigger alert comprises a first client device, and wherein the computing system further comprises program instructions that are executable by the at least one processor to cause the computer system to:
receive, from a second client device, a request to access medical-history information for a given patient, wherein the request includes an identification of the given patient; and
after receiving the request, cause the second client device to present a medical-history visualization for the given patient that is generated based on the anonymized patient data, wherein the medical-history visualization comprises, for each of two or more event types, a respective timeline showing any instance of the event type that has occurred in the given patient's medical history during a given range of time.

11. The computer system of claim 10, wherein the respective timelines for the two or more event types are grouped into two or more categories of event types.

12. A computer-implemented method comprising:
receiving, at a computer system from a data source, anonymized patient data for patients treated by each of a plurality of healthcare providers (HCPs);
applying one or more machine learning techniques to historical patient data associated with past occurrences of a given type of treatment decision in order to train a machine learning model that is configured to (i) receive anonymized patient data for a patient as input and (ii) predict a next time in the future at which the given type of treatment decision is likely to be made for the patient;
analyzing the anonymized patient data for the patients treated by each respective HCP of the plurality of HCPs by inputting the anonymized patient data for each respective patient treated by the respective HCP into the trained machine learning model, wherein the given type of treatment decision is likely to involve a prescription of a given type of pharmaceutical product;
based on the analysis, predicting at least one particular time in the future at which a given HCP of the plurality of HCPs is likely to make the given type of treatment decision for at least one patient;
in response to predicting the particular time in the future at which the given HCP is likely to make the given type of treatment decision for the at least one patient, generating a trigger alert suggesting that the given HCP be visited prior to the particular time in the future to deliver a message related to the given type of treatment decision; and
causing the trigger alert to be sent to a client device associated with a target of the trigger alert.

13. The computer-implemented method of claim 12, wherein the anonymized patient data comprises anonymized identifying information and medical history information for each patient, and wherein the medical history information for each patient comprises information about one or more of drug treatment events, surgery events, radiation events, medical test events, diagnosis events, patient visit events, or side effect events.

14. The computer-implemented method of claim 12, wherein the given type of treatment decision comprises a decision to transition a patient from one stage of treatment to another stage of treatment.

15. The computer-implemented method of claim 12, wherein the trigger alert comprises one or more of an indication of a time for the suggested visit with the given HCP, patient data for the least one patient of the given HCP, or a recommended message to be delivered by the target during the suggested visit with the given HCP.

16. The computer-implemented method of claim 12, wherein causing the trigger alert to be sent to the client device associated with the target of the trigger alert comprises causing the trigger alert to be sent to the client device associated with the target of the trigger alert at a time that is determined based on the particular time in the future.

17. The computer-implemented method of claim 12, wherein the client device associated with the target of the trigger alert comprises a first client device, the method further comprising:

receiving, from a second client device, a request to access medical-history information for a given patient, wherein the request includes an identification of the given patient; and
after receiving the request, causing the second client device to present a medical-history visualization for the given patient that is generated based on the anonymized patient data, wherein the medical-history visualization comprises, for each of two or more event types, a respective timeline showing any instance of the event type that has occurred in the given patient's medical history during a given range of time.

18. A non-transitory computer-readable medium having program instructions stored thereon that are executable by at least one processor of a computer system to cause the computer system to:
apply one or more machine learning techniques to historical patient data associated with past occurrences of a given type of treatment decision in order to train a machine learning model that is configured to (i) receive anonymized patient data for a patient as input and (ii) predict a next time in the future at which the given type of treatment decision is likely to be made for the patient;
receive, from a data source, anonymized patient data for patients treated by each of a plurality of healthcare providers (HCPs);
analyze the anonymized patient data for the patients treated by each respective HCP of the plurality of HCPs by inputting the anonymized patient data for each respective patient treated by the respective HCP into the trained machine learning model, wherein the given type of treatment decision is likely to involve a prescription of a given type of pharmaceutical product;
based on the analysis, predict at least one particular time in the future at which a given HCP of the plurality of HCPs is likely to make the given type of treatment decision for at least one patient;
in response to predicting the particular time in the future at which the given HCP is likely to make the given type of treatment decision for the at least one patient, generate a trigger alert suggesting that the given HCP be visited prior to the particular time in the future to deliver a message related to the given type of treatment decision; and
cause the trigger alert to be sent to a client device associated with a target of the trigger alert.

19. The non-transitory computer-readable medium of claim 18, wherein the trigger alert comprises one or more of an indication of a time for the suggested visit with the given HCP, patient data for the least one patient of the given HCP, or a recommended message to be delivered by the target during the suggested visit with the given HCP.

20. The non-transitory computer-readable medium of claim 18, wherein the program instructions that are executable to cause the computer system to cause the trigger alert to be sent to the client device associated with the target of the trigger alert comprise program instructions that are executable to cause the computer system to cause the trigger alert to be sent to the client device associated with the target of the trigger alert at a time that is determined based on the particular time in the future.

* * * * *